(12) United States Patent
Chiu

(10) Patent No.: US 6,232,476 B1
(45) Date of Patent: May 15, 2001

(54) INTERMEDIATES IN A PROCESS FOR CIS-1-{2-[4-(6-METHOXY-2-PHENYL-1,2,3,4-TETRAHYDRONAPHTHALEN-1-YL) PHENOXY]ETHYL}PYRROLIDINE

(75) Inventor: Charles K. F. Chiu, Guilford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/575,310

(22) Filed: May 19, 2000

Related U.S. Application Data
(60) Provisional application No. 60/135,578, filed on May 24, 1999.

(51) Int. Cl.$^7$ ............................. C07C 15/24; C07C 49/11; C07C 49/16; C07D 317/18
(52) U.S. Cl. ...................... 549/430; 549/453; 568/308; 568/325; 568/335; 568/337; 585/26
(58) Field of Search .................... 549/430, 453; 568/308, 325, 335, 337; 585/26

(56) References Cited

U.S. PATENT DOCUMENTS

| | | | |
|---|---|---|---|
| 3,234,090 | 2/1966 | Huebner et al. | 167/58 |
| 3,274,213 | * 9/1966 | Lednicer et al. | 260/326.5 |
| 3,277,106 | 10/1966 | Bencze et al. | 260/295 |

OTHER PUBLICATIONS

Lednicer, et al., J. Med. Chem., 12, 881 (1969).
Bencze, et al., J. Med. Chem., 10, 138 (1967).
Lednicer, et al., J. Med. Chem., 10, 78 (1967).
Kanapure, S. P., Das, K. G., Bhawal, B. M., Synth. Comm., 1984, 14, 1205–1211.
Lexa, D., Saveant, J. M., Zickler, J., J. Amer. Chem. Soc. 1977, 99, 2786–2790.
Chan, T. H., Brook, M. A., Chaly, T., Synthesis 1983, 203–205.
Gedye, R., Smith, F., Westaway, K., Ali, H., Baldisera, L., Laberge, L., Rousell, J., Tet. Lett., 1986, 279–282.
McMurry, J. E., Kees, K. L., J. Org. Chem., 1977, 42, 2655–2656.

* cited by examiner

*Primary Examiner*—Jane Oswecki
(74) *Attorney, Agent, or Firm*—Peter C. Richardson; Gregg C. Benson; Todd M. Crissey

(57) ABSTRACT

This invention provides an improved process for cis-1-{2-[4-(6-methoxy-2-phenyl-1,2,3,4-tetrahydronaphthalen-1-yl) phenoxy]ethyl}pyrrolidine which is an intermediate for the preparation of (-)cis-6-phenyl-5-[4-(2-pyrrolidin-1-yl-ethoxy)-phenyl]-5,6,7,8-tetrahydronaphthalene-2-ol which is useful for the treatment of osteoporosis.

1 Claim, No Drawings

INTERMEDIATES IN A PROCESS FOR CIS-1-{2-[ 4-(6-METHOXY-2-PHENYL-1,2,3,4-TETRAHYDRONAPHTHALEN-1-YL)PHENOXY]ETHYL}PYRROLIDINE

This application is filed claiming priority from Provisional Application No. 60/135,578 filed on May 24, 1999.

BACKGROUND OF THE INVENTION

1. Field of the Invention

This invention provides an improved process for cis-1-{2-[4-(6-methoxy-2-phenyl-1,2,3,4-tetrahydronaphthalen-1-yl)phenoxy]ethyl}pyrrolidine which is an intermediate for the preparation of (-)cis-6-phenyl-5-[4-(2-pyrrolidin-1-yl-ethoxy)-phenyl]-5,6,7,8-tetrahydronaphthalene-2-ol which is useful for the treatment of osteoporosis.

2. Description of the Related Art

A preparation of (-)cis-6-phenyl-5-[4-(2-pyrrolidin-1-yl-ethoxy)-phenyl]-5,6,7,8-tetrahydronaphthhalene-2-ol is described in U.S. Pat. No. 5,552,241 which is hereby incorporated by reference. This compound is an estrogen agonist and is useful for treatment of conditions caused by estrogen difficiency. U.S. Pat. No. 5,552,241 also describes the synthesis of cis-1-{2-[4-(6-methoxy-2-phenyl-1,2,3,4-tetrahydronaphthalen-1-yl)phenoxy]ethyl}pyrrolidine by hydrogeneration of nafoxidine.

Lednicer, et al., *J. Med. Chem.*, 12, 881 (1969) described estrogen antagonists of the structure

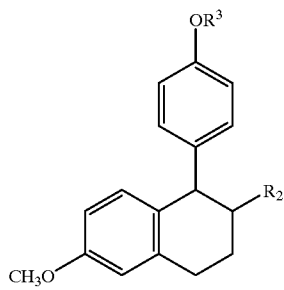

wherein $R^2$ is phenyl or cyclopentyl and $R^3$ is H,

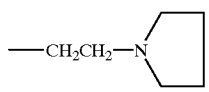

or —CH$_2$CHOHCH$_2$OH.

Bencze, et al., *J. Med. Chem.*, 10, 138 (1967) prepared a series of tetrahydronaphthalenes intended to achieve separation of estrogenic, antifertility and hypocholesterolemic activities. These structures are the general formula

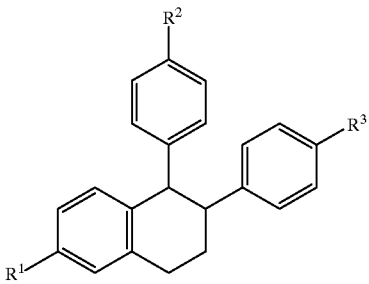

wherein $R^1$ is H or OCH$_3$; $R^2$ is H, OH, OCH$_3$, OPO (OC$_2$H$_5$)$_2$, OCH$_2$CH$_2$N(C$_2$H$_5$)$_2$, OCH$_2$COOH or OCH(CH$_3$) COOH.

U.S. Pat. No. 3,234,090 refers to compounds which have estrogenic and antifungal properties of the formula

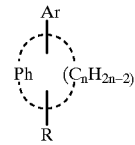

in which Ph is a 1,2-phenylene radical, Ar is a monocyclic carbocyclic aryl group substituted by tertiary amino-lower alkyl-oxy, in which tertiary amino is separated from oxy by at least two carbon atoms, R is hydrogen, an aliphatic radical, a carbocyclic aryl radical, a carbocyclic aryl-aliphatic radical, a heterocyclic aryl radical or a heterocyclic aryl aliphatic radical, the group of the formula —(C$_n$H$_{2n-2}$)— stands for an unbranched alkylene radical having from three to five carbon atoms and carrying the groups Ar and R, salts, N-oxides, salts of N-oxides or quaternary ammonium compounds thereof, as well as procedure for the preparation of such compounds.

U.S. Pat. No. 3,277,106 refers to basic ethers with estrogenic, hypocholesterolemic and antifertility effects which are of the formula

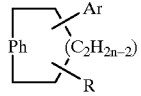

in which Ph is a 1,2-phenylene radical, Ar is a monocyclic aryl radical substituted by at least one amino-lower alkyl-oxy group in which the nitrogen atom is separated from the oxygen atom by at least two carbon atoms, R is an aryl radical, and the portion —(C$_n$H$_{2n-2}$)—stands for lower alkylene forming with Ph a six- or seven-membered ring, two of the ring carbon atoms thereof carry the groups Ar and R, salts, N-oxides, salts of N-oxides and quaternary ammonium compounds thereof.

Lednicer, et al., in J. Med. Chem. 10, 78 (1967) and in U.S. Pat. No. 3,274,213 refer to compounds of the formula

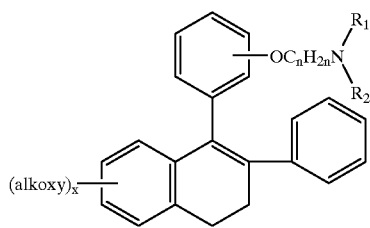

wherein $R_1$ and $R_2$ are selected from the class consisting of lower alkyl and lower alkyl linked together to form a 5 to 7 ring member saturated heterocyclic radical.

REFERENCES

1. Kanapure, S. P.; Das, K. G.; Bhawal, B. M. *Synth. Comm.* 1984, 14, 1205–1211.
2. Lexa, D.; Saveant, J. M.; Zickler, J. *J. Amer. Chem. Soc.* 1977, 99, 2786–2790.
3. Chan, T. H.; Brook, M. A.; Chaly, T. *Synthesis* 1983, 203–205.
4. Gedye, R.; Smith, F.; Westaway, K.; Ali, H.; Baldisera, L.; Laberge, L.; Rousell, J. *Tet Lett.* 1986, 27, 279–282.
5. McMurry, J. E.; Kees, K. L. *J. Org. Chem.* 1977, 42, 2655–2656.

SUMMARY OF THE INVENTION

This invention provides intermediate compounds which are useful for the preparation of (-)cis-6-phenyl-5-[4-(2-pyrrolidin-1-yl-ethoxy)-phenyl]-5,6,7,8-tetrahydronaphthalene-2-ol. These compounds include: 3-(2-Bromo-5-methoxy-phenyl)-1-phenyl-propan-1-one; 2-[2-(2-Bromo-5-methoxy-phenyl)-ethyl]-2-phenyl-[1,3]dioxolane; 3-[2-(4-Benzyloxy-benzoyl)-5-methoxy-phenyl]-1-phenyl-propan-1-one; and 4-(4-Benzyloxy-phenyl)-7-methoxy-3-phenyl-1,2-dihydro-naphthalene; and (4-Benzyloxy-phenyl)-{4-methoxy-2-[2-(2-phenyl-[1,3]dioxolan-2-yl)-ethyl]-phenyl}-methanone.

This invention also provides a method of preparing Cis-1-{4-[6-methoxy-2-phenyl-1,2,3,4-tetrahydronaphthalene-1-yl)phenoxy]ethyl}pyrrolidine which comprises the following steps:

1) 2-Bromo-5-methoxy-toluene is brominated to provide 1-bromo-2-bromomethyl-4-methoxybenzene;
2) The product of step 1 is used to alkylate benzoyl acetate ethyl ester followed by decarboxylation to provide 3-(2-bromo-5-methoxyphenyl)-1-phenyl-propan-1-one;
3) The product of step 2 is reacted with ethylene glycol to produce 2-[2-(2-bromo-5-methoxyphenyl)-ethyl]-2-phenyl-ethyl]-2-phenyl-[1,3]dioxolane;
4) The product of step 3 undergoes metal-halogen exchange with n-butyl lithium and is reacted with 4-benzyloxy benzonitrile to produce 2-[2-(2-(4-benzyloxybenzoyl)-5-methoxy phenyl)-ethyl]-2-phenyl-[1,3]-dioxolane which is subjected to acid hydrolysis of the 1,3 dioxolane to provide 3-[2-(4-benzyloxybenzoyl)-5-methoxyphenyl]-1-phenyl propan-1-one;
5) The product of step 4 is treated with titanium (III) chloride and zinc-copper couple to produce 4-(4-benzyloxyphenyl)-7-methoxy-3-phenyl-1,2-dihydronaphthalene;
6) The product of step 5 is hydrogenated and treated with triphenyl phosphine, DEAD and 1-(2-hydroxyethyl) pyrolidine to produce 1-{2-[4-(6-methoxy-2-phenyl-1,2,3,4-tetrahydronaphthalene-1-yl)-ethyl}-pyrrolidine.

This invention also provides a method of reacting

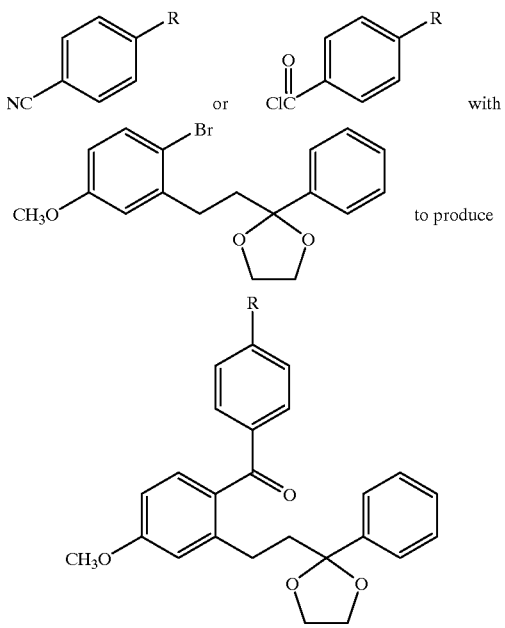

wherein R is a protected phenol or

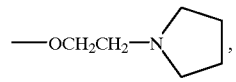

which comprises reacting 2-[2-(2-bromo-5-methoxyphenyl)-ethyl]-2-phenyl-[1,3]dioxolane with butyl lithium followed by reaction with

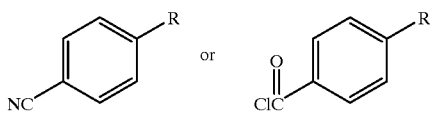

DETAILED DESCRIPTION OF THE INVENTION

This invention provides a new synthesis of cis-1-{2-[4-(6-methoxy-2-phenyl-1,2,3,4-tetrahydronaphthalen-1-yl)phenoxy]ethyl}pyrrolidine as shown below.

Acronyms used in this description are defined as follows:

| | |
|---|---|
| NBS | N-bromosuccinimide |
| AIBN | 2,2'-Azobisisobutyronitrile |
| TMSCl | Trimethyl chloro silane |
| THF | tetrahydrofuran |
| PPTS | pyridine p-toluene sulfonate |
| DEAD | Diethyl azodicarboxylate |
| DME | Dimethoxy ethane |

The term "protected phenol" includes optional benzyloxy groups substituted with alkoxy, nitro or halogen, and other acceptable alcohol protecting groups.

Synthesis of CIS-1-{2-[4-(6-Methoxy-2-phenyl-1,2,3,4-Tetrahydronaphthalen-1-yl)phenoxy]ethyl}pyrrolidine

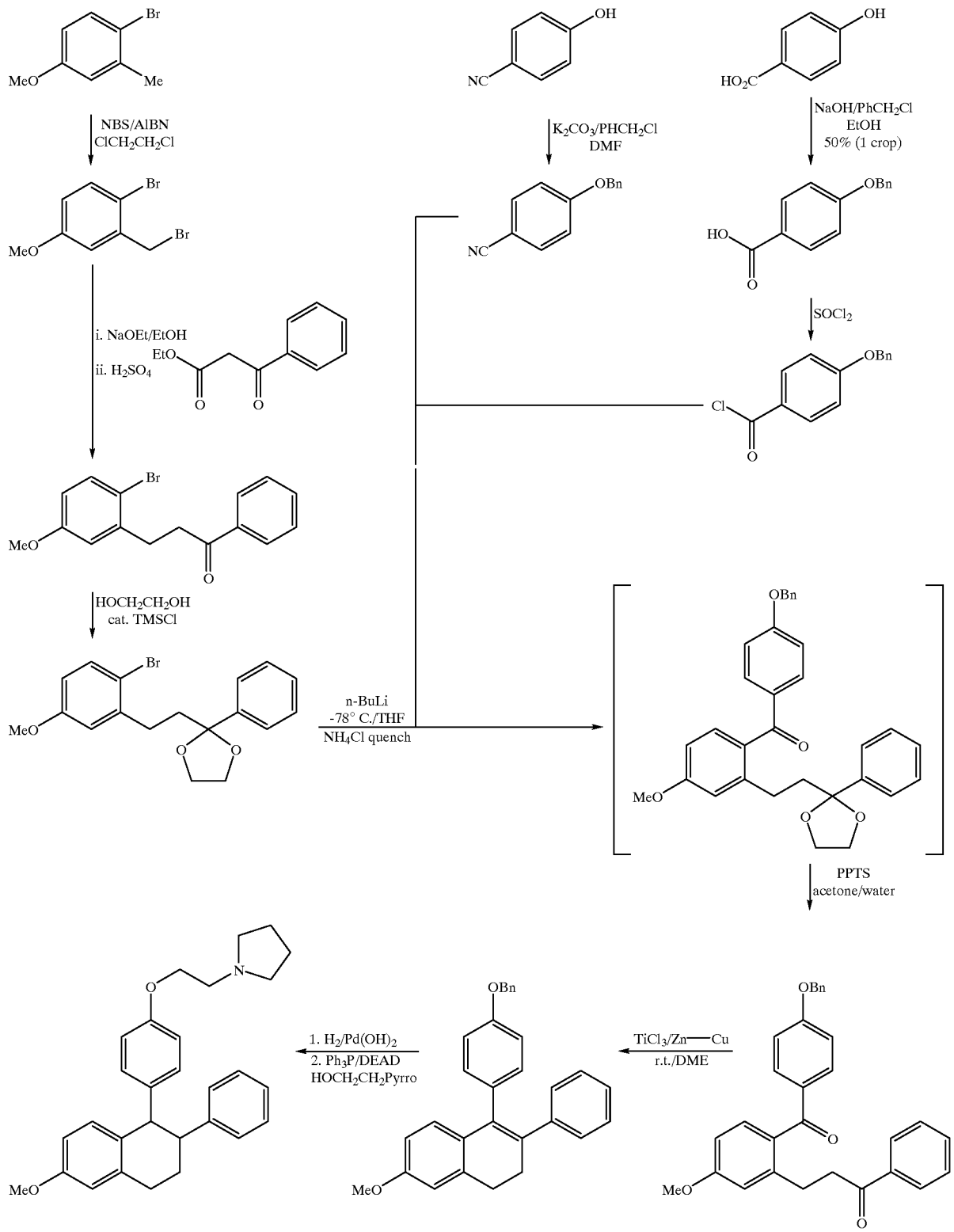

The synthesis begins with bromination[1] of 2-bromo-5-methoxy-toluene to provide the benzyl bromide 1-Bromo-2-bromomethyl-4-methoxy-benzene. Alkylation of ethyl benzoylacetate[2] with the benzyl bromide followed by decarboxylation leads to the ketone 3-(2-Bromo-5-methoxy-phenyl)-1-phenyl-propan-1-one, which is protected[3] as the ketal 2-[2-Bromo-5-methoxy-phenyl)-2-phenyl-[1,3] dioxolane. Metal-halogen exchange of ketal 2-[2-Bromo-5-methoxy-phenyl)-2-phenyl-[1,3]dioxolane provides an aryllithium species, which adds readily to either 4-benzyloxybenzoate or 4-benzoxy-benzontrile[4] and furnishes the diketone 3-[2-(4-Benzyloxy-benzoyl)-5-methoxy-phenyl]-1-phenyl-propan-1-one upon acidic work-up. The diketone undergoes a titanium mediated McMurry type coupling[5] to provide the alkene 4-(4-Benzyloxy-phenyl)-7-methoxy-3-phenyl-1,2-dihydro-naphthalene, which possesses the carbon framework of cis-1-{2-[4-(6-methoxy-2-phenyl-1,2,3,4-tetrahydronaphthalen-1-yl)phenoxy]ethyl}pyrrolidine with all the functional groups in place. A palladium catalyzed hydrogenation achieves the reduction of the olefinic double bond and deprotection of the benzyl ether in one pot. The introduction of the N-ethyl-pyrrolidino side-chain is achieved under Mitsunobu conditions to afford 1-{2-[4-(6-Methoxy-2-phenyl-1,2,3,4-tetrahydronaphthalen-1-yl)-phenoxy]-ethyl}-pyrrolidine, the key precursor to cis-1-{2-[4-(6-methoxy-2-phenyl-1,2,3,4-tetrahydronaphthalen-1-yl)phenoxy]ethyl}pyrrolidine. This compound is converted to cis-6-phenyl-5-[4-(2-pyrrolidin-1-yl-ethoxy)-phenyl]-5,6,7,8-tetrahydronaphthalene-2-ol with HBr as described in U.S. Pat. No. 5,552,241.

EXAMPLES

Example 1
1-Bromo-2-Bromomethyl-4-Methoxy-Benzene
Reference: Synthetic Communications, 1984, 1205–1211

To a solution of 2-bromo-5-methoxytoluene (50 g, 0.25 mol) in dichloroethane (375 ml), N-bromosuccinimide (48.8 g, 0.275 mol) and AIBN (1.36 g) were added and the reaction was refluxed for 4 h. The cooled solution was filtered and the solvent was evaporated to give a weight of 44.8 g crude 1-Bromo-2-bromomethyl-4-methoxy-benzene (64% yield).
This compound was used in next step without further purification.

Example 2
3-(2-Bromo-5-Methoxy-Phenyl)1-Phenyl-Propan-1-One
Reference: JACS, 1977,2786

To sodium ethoxide (5.72 g, 84 mmol) in 50 ml of anhydrous ethanol was added 14.8 g (77 mmol) of ethyl benzoylacetate with stirring. The reaction mixture was then brought to a gentle reflux and 19.6 g (70 mmol) of 1-Bromo-2-bromomethyl-4-methoxy-benzene in 20 ml of ethanol was added over 20 min. The reaction mixture was refluxed for 2 h. The reaction mixture was cooled, filtered and concentrated. The concentrated mixture was subjected to acid hydrolysis and decarboxylation by refluxing for overnight in a solution containing 40 ml of glacial acetic acid, 5 ml of concentrated sulfuric acid, and 10 ml of water. The reaction mixture was then neutralized with 10% NaOH and extracted with methylene chloride. The extracts were concentrated to give a weight of 19.43 g crude 3-(2-Bromo-5-methoxy-phenyl)-1-phenyl-propan-1-one (yield: 87%). This compound was used in next step without further purification.

Example 3
2-[2-(2-Bromo-5-Methoxy-Phenyl)-Ethyl]-2-Phenyl-[1,3] Dioxolane
Reference: Synthesis, 1983,203

To a solution of crude 3-(2-Bromo-5-methoxy-phenyl)-1-phenyl-propan-1-one (19.43 g, 61 mmol) in dry ethylene glycol (300 ml) under a $N_2$ atmosphere was added chlorotrimethylsilane (31 ml, 0.25 mol). The reaction was stirred at room temperature for 1 h. A 5% aqueous $NaHCO_3$ (300 ml) was added. The mixture was extracted with diisopropyl ether, and the extracts were washed with brine. The combined ether extracts were dried with $Na_2SO_4$ and the solvent was removed under reduced pressure to produce a weight of 21.52 g crude 2-[2-(2-Bromo-5-methoxy-phenyl)-ethyl]-2-phenyl-[1,3]dioxolane (yield: 97%).

Example 4
4-Benzyloxy-Benzonitrile
Reference: Tetrahedron Lett. 1986, 279–282

To a solution of 4-cyanophenol (25 g, 0.21mol) and $K_2CO_3$ (138 g, 1 mol) in DMF (300 ml) was added benzyl chloride (27.91 g, 0.22 mol) in one portion. The resulting mixture was stirred at room temperature overnight. The suspension was filtered and the filtrate was poured into iced water. The resulting solid was collected to provide a weight of 43.5 g product (yield: 99%).

Example 5
3-[2-(4-Benzyloxy-Benzoyl)-5-Methoxy-Phenyl]-1-Phenyl-Propan-1-One A solution of 2-[2-(2-Bromo-5-methoxy-phenyl)-ethyl]-2-phenyl-[1,3]dioxolane (0.9 g, 2.5 mmol) in 10 ml of dry THF was cooled to −78° C. and n-BuLi (2.5 M in hexane, 1 ml) was added dropwise. The solution was stirred at −78° C. for 2 h and 4-benzyloxy-benzonitrile (0.575 g, 2.75 mmol) in 2 ml of THF was added. The mixture was allowed to warm to room temperature and refluxed overnight. The solution was then quenched with sat. $NH_4Cl$ and the solvent was evaporated. A solution of the residue in 20 ml of wet acetone, 5 ml of $H_2O$ containing PPTS (188 mg, 0.75 mmol) was refluxed overnight. Regular workup and column purification afforded an unoptimized weight of 0.8 g 3-[2-(4-Benzyloxy-benzoyl)-5-methoxy-phenyl]-1-phenyl-propan-1-one.

Example 6
(4-Benzyloxy-Phenyl)-7-Methoxy-3-Phenyl-1,2-Dihydro-Naphthalene
Reference: JOC, 1977, 2656

$TiCl_3$ (2.062 g, 13 mmol) and Zn—Cu couple (2.02 g, 30.8 mmol) were placed in a 200 ml round bottom flask under N2. Anhydrous dimethoxyethane (40 ml) was added and the mixture was refluxed for 1 h.
Note: The Zn—Cu couple is prepared by adding zinc dust (9.8 g, 150 mmol) to 40 ml of deoxygenated water, purging the slurry with N2 gas for 15 min, and than adding CuSO4 (0.75 g, 4.7 mmol). The black slurry was filtered under N2, washed with deoxygenated $H_2O$, acetone, ether, and then stored under $N_2$.

3-[2-(4-Benzyloxy-benzoyl)-5-methoxy-phenyl]-1-phenyl-propan-1-one (540 mg, 1.2 mmol) in 80 ml of DME was added to the refluxing slurry and the resulting mixture was refluxed for 15 min. The suspension was filtered and the solvent was evaporated to give a weight of 0.45 g 4-(4-Benzyloxy-phenyl)-7-methoxy-3-phenyl-1,2-dihydro-naphthalene (yield: 90%, structure was confirmed by X-ray).

Example 7
1-{2-[4-(6-Methoxy-2-Phenyl-1,2,3,4-Tetrahydro-Naphthalen-1-yl)-Ethyl}-Pyrrolidine 4-(4-Benzyloxy-phenyl)-7-methoxy-3-phenyl-1,2-dihydro-naphthalene (0.45 g, 1.08 mmol) was dissolved in a mixture of EtOH (15 ml) in a Paar bottle. $Pd(OH)_2$ (0.3 g) in 2 ml of H2O was added and the mixture was shaken under H2 (50 psi) at room temperature. The solution was filtered and treated with same equivalent of triphenylphosphine, DEAD and 1-(2-hydroxyethyl)pyrrolidine. Normal workup gave 1-{2-[4-(6-Methoxy-2-phenyl-1,2,3,4-tetrahydro-naphthalen-1-yl)-ethyl}-pyrrolidine.

What is claimed is:

1. A compound selected from the group consisting of 3-(2-Bromo-5-methoxy-phenyl)1-phenyl-propan-1-one; 2-[2-(2-Bromo-5-methoxy-phenyl)-ethyl]-2-phenyl-[1,3] dioxolane; 3-[2-(4-Benzyloxy-benzoyl)-5-methoxy-phenyl]-1-phenyl-propan-1-one; 4-(4-Benzyloxy-phenyl)-7-methoxy-3-phenyl-1,2-dihydro-naphthalene; and (4-Benzyloxy-phenyl)-{4-methoxy-2-[2-(2-phenyl-[1,3] dioxolan-2-yl)-ethyl]-phenyl}-methanone.

* * * * *